United States Patent [19]

Tezuka et al.

[11] Patent Number: 5,571,516

[45] Date of Patent: Nov. 5, 1996

[54] BATH MEDICINE

[75] Inventors: Hiroshi Tezuka; Kazuyo Tezuka, both of Tokyo, Japan

[73] Assignee: K.K. Nendo Science Laboratory, Tokyo, Japan

[21] Appl. No.: 294,556

[22] Filed: Aug. 23, 1994

[30] Foreign Application Priority Data

Aug. 24, 1993 [JP] Japan .................................. 5-230860

[51] Int. Cl.$^6$ ....................................... A61K 7/48
[52] U.S. Cl. ..................... 424/401; 424/195.1; 514/944; 514/949
[58] Field of Search ................................ 424/401, 195.1; 514/949, 817, 848, 844–47, 195.1, 937, 944

[56] References Cited

U.S. PATENT DOCUMENTS

| | | | |
|---|---|---|---|
| 4,108,984 | 8/1978 | Sato | 424/69 |
| 4,460,488 | 7/1984 | Grollier et al. | 424/70 |
| 4,569,839 | 2/1986 | Grollier et al. | 424/70 |
| 4,717,735 | 1/1988 | Strem | 514/949 |
| 4,735,802 | 4/1988 | Le | 514/949 |
| 5,139,771 | 8/1992 | Gerstein | 424/401 |

OTHER PUBLICATIONS

Hiromu Tezuka, *Chemical Abstracts*, vol. 121, #18108 (1992).

*Primary Examiner*—Jyothsna Venkat
*Attorney, Agent, or Firm*—Koda and Androlia

[57] ABSTRACT

A bath medicine is provided which comprises a water swelling gel of a natural or synthetic sodium montmorillonite or a composite of the water swelling gel and urea as the main component, and one or more components selected from among humectants, oils, fats, crude drugs, extracts, enzymes and other medicines, and which always maintains the wet state; preferably, the humectants being 1,3-butylene glycol, sodium lactate, etc., the oils and fats being jojoba oil, squalane oil, rice germ oil, etc., the crude drugs being Rehmannia root extract, peach leaf extract, loquat leaf extract, etc., the extracts being fermented rice extract, orris extract, etc., the enzymes being trypsin, papain, etc., and the other medicinal ingredients being nucleic acid, deoxyribonucleic acid, peptides obtained by the hydrolysis or enzymolysis of silkworm yarns or silk proteins, and which exhibits a remarkable effect on atopic dermatitis, pruritus cutaneus senilis, etc.

3 Claims, No Drawings

BATH MEDICINE

DETAILED DESCRIPTION OF THE INVENTION

1. Field of Industrial Application

The present invention relates to a bath medicine comprising a water swelling gel of a natural or synthetic sodium montmorillonite or a composite of the water swelling gel and urea. More particularly, the invention relates to a novel bath medicine characterized by always maintaining the wet state and having unique usages such that it is applied to a user's body prior to bathing and the user bathes in such a state to dissolve the medicine in a high concentration around the body in the bath to thereby improve the effect of the bath medicine, or alternatively the bath medicine is dispersed and suspended in the bath and, after bathing, the user dries the wetted body without wiping away the adherent medicine.

2. Prior Art

Various bath medicines have been proposed and some of them have a considerable effect of warming the body and keeping the body warm by improving the blood circulation in addition to the effect of cleaning and activating the skin.

Compositions to be particularly noted are ones which comprise a water swelling clay mineral containing inorganic salts such as magnesium sulfate and sodium hydrogencarbonate and liquid components such as a humectant, oil and fat and which are estimated to be excellent bath medicines, since they have high solubility, non-aggregating properties and high fluidity.

According to the inventor's follow-up test, however, it was found that although the inorganic salts exhibit an excellent effect of warming the skin as in natural hot springs, the humectants, oils and fats contained in such bath medicines gradually lower the fluidity and solubility of the powder due to the deliquescence inherent in the inorganic salts to deteriorate the quality of the bath medicine with the lapse time. Namely, the inventors have found that the inorganic salts produce a negative synergistic effect with other components incorporated in the bath medicine with the lapse of time.

PROBLEM TO BE SOLVED BY THE INVENTION

The present invention has been completed under these circumstances. Namely, the inventors have found that a water swelling gel of a natural or synthetic sodium montmorillonite having the most excellent water swelling properties among clay minerals or a composite of the water swelling gel and urea has remarkable solubility, non-aggregating properties, skin-cleaning effect and skin-warming effect and particularly a high quality stability even after the lapse of time, thus providing a novel bath medicine prepared by adding organic substances to the above-described gel or composite.

Most of ordinary bath medicines are in powdery form, and thrown into warm water in a bathtub prior to bathing. On the contrary, the bath medicine of the present invention is characterized by mainly comprising a water swelling gel of sodium montmorillonite or a composite of the water swelling gel and urea and always maintaining the wet state.

The bath medicine of the present invention can be used in such a manner that it is applied to a user's body prior to bathing and the user immerse the body in warm water or the like to gradually dissolve and disperse the medicine from the surface of the body. Thus the highest concentration of the medicine is realized around the body and the water surrounding the body becomes milky to keep a unique medicinal effect around the body for a long time. Another advantage is that since the bath medicine is dissolved out of the pack applied to the user's body by the action of the user himself, sufficient relaxation and fun are also provided.

The bath medicine of the present invention which comprises the water swelling gel of sodium montmorillonite or the composite of the gel and urea effectively acts on the wastes formed by keratinization of the skin cells to remove them by enclosing them. The bath medicine also encloses the sebum secreted through the sebaceous glands and sweat secreted through the sweat glands to clean the skin. Particularly, it realizes the feeling of comfortableness and moistness together with a humectant, oil and fat and, in addition, it is effective in curing eczema, dermatitis and the like. The water swelling gel is dispersed in the form of ultrafine particles in the bath, and the ultrafine particles carrying the humectant, oil, fat and other ingredients such as a crude drug penetrate into the skin. The bath medicine of the present invention has also an effect similar to that of a cream or lotion which is to be directly applied to the skin, and it is retained on the skin to produce the medicinal effect as long as possible.

MEANS FOR SOLVING THE PROBLEM

The gist of the present invention resides in a bath medicine which comprises:

a water swelling gel of a natural or synthetic sodium montmorillonite or a composite of the water swelling gel and urea as the main component, and added thereto, one or more components selected from among humectants, oils, fats, crude drugs, enzymes, extracts and other medicines, and which is capable of always maintaining the wet state.

The bath medicine of the present invention comprises, as the main component, a water swelling gel of a natural or synthetic sodium montmorillonite or a composite of the water swelling gel and urea, taking advantage of the properties thereof to easily react with various organic matters and to enclose them. There has been no attempt at all to use a water swelling gel of sodium montmorillonite as the bath medicine.

A humectant is incorporated into the bath medicine in order to keep the moist state thereof. The humectant is selected from among 1,3-butylene glycol, sodium lactate, lactic acid, sodium DL-pyrrolidonecarboxylate, glycerol, propylene glycol and other polyhydric alcohol, and saccharides such as sorbitol. These are usable either singly or a combination of two or more of them.

The water swelling gel of sodium montmorillonite is effective in emulsion-dispersing oils and fats. Emulsion-dispersed oils and fats are usually effective in curing diseases such as atopic dermatitis and pruritus cutaneus senilis.

The oils and fats are selected from among jojoba oil, squalane oil, rice germ oil, wheat germ oil, vitamin E, carrot oil, olive oil, avocado oil, peppermint oil, almond oil, hinoki oil, orange oil, lavender oil and rosemary oil. They are used either singly or a combination of two or more of them.

These oils and fats have other effects peculiar to them. Namely, jojoba oil softens the skin and inhibits hypersecretion of the sebum; the squalane oil has a skin-penetrating effect; rice germ oil contains effective ingredients such as oryzanol, vitamin E and sterols in high concentrations, and its antioxidizing effect is improved in the presence of proteins and amino acids; and wheat germ oil containing vitamin F is effective in curing various skin diseases and improves the activity of capillaries by synergism with vitamin E to activate the skin cells.

The crude drugs are effective in ameliorating atopic dermatitis, pruritus cutaneus senilis, etc. They are supported by the water swelling gel of sodium montmorillonite as the carrier and adhere to the skin surface.

One or more crude drugs are selected from among Rehmannia root, peach leaf, loquat leaf, saponaria, scutellaria root, chammomille, hypericum, sage, sambucus, witch hazel, burdock root, thyme, gambir, isodonis, clove, horsetail, mulberry bark, jasmine, fennel, ginger, bitter orange peel, gardenia, dried orange peel, ginseng, mugwort, jujube, aloe, Angelica root and phellodendron extracts.

The respective crude drugs have the following effects unique to them, in addition to the above-described effects of ameliorating the skin diseases:

Rehmannia root extract: humectant and cell-activating effects,
peach leaf extract: antimicrobial and antiphlogistic effects,
loquat leaf extract: humectant, antiphlogistic, antimicrobial and astringent effects,
saponaria extract: cleansing, cleaning and diaphoretic effects,
scutellaria root extract: antiphlogistic, astringent and humectant effects,
chamomille extract: humectant, antiphlogistic, antimicrobial and antipruritic effects,
hypericum extract: astringent, sunscreening, humectant and skin-cleaning effects,
sage extract: anti-inflammatory and antimicrobial effects,
sambucus extract: astringent and analgesic effects,
witch hazel extract: astringent and antiseptic effects,
burdock root extract: humectant effect,
thyme extract: humectant, antimicrobial, scar formation-inhibiting and hemostatic effects,
gambir extract: astringent and antiallergic effects,
isodonis extract: antimicrobial and blood circulation-accelerating effects,
clove extract: antimicrobial and blood circulation-accelerating effects,
horsetail extract: humectant, antiphlogistic, astringent, cell-activating hemostatic and antisudorific effects,
funnel extract: humectant effect,
ginger extract: hair growth-accelerating and blood circulation-accelerating effects,
gardenia extract: anti-inflammatory effect,
phellodendron extract: antimicrobial, astringent, anti-inflammatory and humectant effects,
ginseng extract: humectant, blood circulation-accelerating and cell-activating effects,
jujube extract: humectant, antiphlogistic and skin-regenerating effects, and
aloe extract: vulnerary, humectant, skin-softening, beautifying, sunscreening and cell-activating effects The extracts used for improving the warming effect are selected from among fermented rice extract, orrisroot extract, glycyrrhiza extract and garlic extract. They are used either singly or in combination of two or more of them. Enzymes used for improving the skin-cleansing effect are one or more enzymes selected from among proteases including trypsin, papain and lysozyme. One or more other medicinal ingredients are selected from among nucleic acid, deoxyribonucleic acid and potassium or sodium salts of them, phosphoric acid salts, ribonucleic acid and sodium salt thereof, glycylrrhizic acid and potassium salt thereof, and peptides and amino acids obtained by the hydrolysis or enzymolysis of silkworm yarns or silk proteins.

They are bound to sodium montmorillonite by interlaminar bonding. The binding of the peptides or amino acids obtained by the hydrolysis or enzymolysis of silkworm yarns or silk proteins having amino groups is particularly easy.

As compared with a case wherein such an ingredient is dispersed as one of the ingredients of the bath medicine, it is more easily kept in the sodium montmorillonite by the interlaminar bonding, and they are dispersed in the form of very fine particles in the whole bath, water, so that they are brought into contact with the skin of the whole body. Therefore, the effects such as humectant, skin cell-activating and ultraviolet absorbing effects are expected.

It is unnecessary to take a shower after using the bath medicine of the present invention. Namely, it will suffice when the body is wiped with a towel after bathing without a shower. It will be apparent from the Examples given below that the formulation of the bath medicine is very close to that of a cream or lotion to be directly applied to the skin. Therefore, the bath medicine must be kept on the skin as long as possible to realize the effect of the ingredients, which is one of the features of the present invention.

EXAMPLES

The following Examples will further illustrate the present invention, which by no means limit the invention.

Example 1

A bath medicine expected to be effective on mainly atopic skin diseases is as follows:

| Ingredient | Amount (pt. by wt.) |
| --- | --- |
| purified water | 25.5 |
| sodium montmorillonite | 7.5 |
| urea | 3.0 |
| kaolin | 19.0 |
| concentrated glycerol | 23.0 |
| sugar ester | 2.0 |
| squalane | 2.0 |
| rice germ oil | 3.0 |
| sodium lactate | 3.0 |

-continued

| Ingredient | Amount (pt. by wt.) |
|---|---|
| oligopeptide formed by enzymolyzing silk yarn protein | 2.0 |
| sodium DL-pyrrolidonecarboxylate | 4.0 |
| 1,3-butylene glycol | 2.5 |
| fermented rice extract | 2.0 |
| loquat leaf extract | 1.5 |
| in total: | 100.0 |

Example 2

This formulation is used for beautifying the whole body, which is to be applied to the body as a body pack outside the bath tub to obtain the effect of the pack. Then, the body is immersed in hot bath water without washing away the pack to obtain the effect of the bath medicine.

| Ingredient | Amount (pt. by wt.) |
|---|---|
| purified water | 9.2 |
| sodium montmorillonite | 5.5 |
| urea | 3.0 |
| 1,3-butylene glycol | 3.0 |
| sodium lactate solution | 2.0 |
| oligopeptide formed by enzymolyzing silk yarn protein | 2.0 |
| sodium DL-pyrrolidonecarboxylate | 3.5 |
| kaolin | 14.5 |
| glycerol | 18.0 |
| rice germ oil | 2.5 |
| jojoba oil | 1.5 |
| lysozyme | 1.8 |
| scutellaria root extract | 2.0 |
| in total: | 100.0 |

Example 3

This formulation mainly comprises crude drugs, which is to be applied to the body as a body pack outside the bath tub and then to be washed away by immersing the body in the bath water or by taking a shower. It is usable also as an ointment.

| Ingredient | Amount (pt. by wt.) |
|---|---|
| purified water | 37.0 |
| sodium montmorillonite | 6.5 |
| urea | 1.0 |
| 1,3-butylene glycol | 2.0 |
| sodium lactate solution | 2.0 |
| kaolin | 14.5 |
| glycerol | 19.0 |
| sorbitol solution | 6.5 |
| rice germ oil | 2.6 |
| jojoba oil | 1.5 |
| fermented rice extract | 1.0 |
| scutellaria root extract | 2.0 |

-continued

| Ingredient | Amount (pt. by wt.) |
|---|---|
| loquat extract | 2.5 |
| mulberry bark extract | 2.0 |
| in total: | 100.0 |

We claim:
1. A bath medicine comprising:

| Ingredient | Amount (pt. by wt.) |
|---|---|
| purified water | 25.5 |
| sodium montmorillonite | 7.5 |
| urea | 3.0 |
| kaolin | 19.0 |
| concentrated glycerol | 23.0 |
| sugar ester | 2.0 |
| squalane | 2.0 |
| rice germ oil | 3.0 |
| sodium lactate | 3.0 |
| oligopeptide formed by enzymolyzing silk yarn protein | 2.0 |
| sodium DL-pyrrolidonecarboxylate | 4.0 |
| 1, 3-butylene glycol | 2.5 |
| fermented rice extract | 2.0 |
| loquat leaf extract | 1.5. |

2. The bath medicine comprising:

| Ingredient | Amount (pt. by wt.) |
|---|---|
| purified water | 9.2 |
| sodium montmorillonite | 5.5 |
| urea | 3.0 |
| 1, 3-butylene glycol | 3.0 |
| sodium lactate solution | 2.0 |
| oligopeptide formed by enzymolyzing silk yarn protein | 2.0 |
| sodium DL-pyrrolidonecarboxylate | 3.5 |
| kaolin | 14.5 |
| glycerol | 18.0 |
| rice germ oil | 2.5 |
| jojoba oil | 1.5 |
| lysozyme | 1.8 |
| scutellaria root extract | 2.0. |

3. The bath medicine comprising:

| Ingredient | Amount (pt. by wt.) |
|---|---|
| purified water | 37.0 |
| sodium montmorillonite | 6.0 |
| urea | 1.0 |
| 1, 3-butylene glycol | 2.0 |
| sodium lactate solution | 2.0 |
| kaolin | 14.5 |
| glycerol | 19.0 |
| sorbitol solution | 6.5 |
| rice germ oil | 2.6 |
| jojoba oil | 1.5 |
| fermented rice extract | 1.0 |
| scutellaria root extract | 2.0 |
| loquat extract | 2.5 |
| mulberry bark extract | 2.0. |

* * * * *